(12) United States Patent
Hilleary et al.

(10) Patent No.: US 7,068,052 B2
(45) Date of Patent: *Jun. 27, 2006

(54) METHODS AND SYSTEMS FOR AUTOMATED PIPELINE TESTING

(75) Inventors: Thomas N. Hilleary, Kansas City, MO (US); Perry B. Peden, Jr., Bonner Springs, KS (US)

(73) Assignee: NTG, Inc., Lenexa, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/873,473

(22) Filed: Jun. 22, 2004

(65) Prior Publication Data

US 2004/0232924 A1 Nov. 25, 2004

Related U.S. Application Data

(63) Continuation-in-part of application No. 10/096,200, filed on Mar. 12, 2002, now Pat. No. 6,822,432.

(60) Provisional application No. 60/300,348, filed on Jun. 22, 2001.

(51) Int. Cl.
*G01R 31/02* (2006.01)
*G01R 27/08* (2006.01)
*G01N 17/04* (2006.01)

(52) U.S. Cl. .................. 324/700; 324/72; 205/777

(58) Field of Classification Search ............. 324/72, 324/72.5, 71.2, 323, 368, 347, 348, 73.1; 455/423, 450, 67.11; 205/777

See application file for complete search history.

(56) References Cited

U.S. PATENT DOCUMENTS

| | | | | |
|---|---|---|---|---|
| 5,325,047 A | * | 6/1994 | Kempton | 324/72 |
| 5,587,707 A | * | 12/1996 | Dickie et al. | 340/870.09 |
| 5,711,001 A | * | 1/1998 | Bussan et al. | 455/432.1 |
| 5,785,842 A | * | 7/1998 | Speck | 205/777.5 |
| 5,939,982 A | * | 8/1999 | Gagnon et al. | 340/539.17 |
| 6,249,122 B1 | * | 6/2001 | Vail et al. | 324/368 |
| 6,538,577 B1 | * | 3/2003 | Ehrke et al. | 340/870.02 |
| 6,553,336 B1 | * | 4/2003 | Johnson et al. | 702/188 |
| 6,822,432 B1 | * | 11/2004 | Hilleary | 324/72 |
| 6,990,395 B1 | * | 1/2006 | Ransom et al. | 700/295 |

* cited by examiner

*Primary Examiner*—Anjan Deb
(74) *Attorney, Agent, or Firm*—Armstrong Teasdale LLP

(57) ABSTRACT

A method for testing a cathodic protection system is disclosed where the system includes a cathodic protection rectifier configured to apply a voltage across a pipeline and a reference point. The method includes measuring a magnitude of an output voltage of the cathodic protection rectifier, transmitting to a site remote from the rectifier, the measured output voltage magnitude using a cellular control channel, receiving the transmitted measurement at the remote site, and using the transmitted measurement to determine whether the cathodic protection system is operational.

23 Claims, 14 Drawing Sheets

Major Components of the Cellular Telephone Network

Network Overview

Active Sites

34 Sites matched this Search. Displaying Page 2 of 2  Time: 0 second(s).

| Status | Site ID | Site Description | Last Contact |
|---|---|---|---|
| ☼ ☎ ‖ | MB287 CP257 | Lowery Rd. & A.C.F.C. | 2/24/01 2:59:53PM CST |
| | MCD #10 REC #12 | McDonald Is. Well #10 Rectifier #12 | 2/24/01 2:59:53PM CST |
| | MCD #12 REC #13 | McDonald Is. Well #12 Rectifier #13 | 2/24/01 2:59:53PM CST |
| | MCD #13 REC #14 | McDonald Is. Well #13 Rectifier #14 | 2/24/01 2:59:53PM CST |

Advanced Search

Find Sites by Status
- Status: [Active ▾]
- Evaluation Only Status: [-Any- ▾]
- ☐ Sites In Alarm
- ☐ Sites Not Responding
- ☐ Sites Not Yet Installed
- Allow Config Key Update Status: [-Any- ▾]
- Unit Installation Status of Site: [-Any- ▾]
- Op State is: [-Any- ▾]

Find Sites by Owner
- Owner: [-Any Owner- ▾]

Find Sites by Text Search
- Search ⦿ Site ID  for [        ]
-         ○ Site Description Find Sites by Group
- Group: [-Any Owner- ▾]

[Search Now]

FIG. 11A

Mcdonald Is. Well #5 Rectifier #8

Operational Info

Description: Mcdonald Is. Well #5 Rectifier #8
Service Status: Active

Operating State: Run

Force To Run Status: Inactive

Logical Input Status

| | Channel | Status | Received |
|---|---|---|---|
| 0 | Power Fail | Normal | 37 days ago. |
| 1 | Channel 01 | Normal | 37 days ago. |
| 2 | Channel 02 | Normal | 37 days ago. |

Physical Input Status

| | Channel | Status | Received | Analog Value |
|---|---|---|---|---|
| 1 | Channel 01 | Normal | 5 hours ago. | 13:19 |
| 2 | Channel 02 | Normal | 5 hours ago. | 5.149 |

Recent Network Activity

Shown below is all network traffic to and from this site in the past 60 days.

09/13/01  2:53:47AM PDT R> Analog Input Value: [2: (5.149)]
09/13/01  2:53:47AM PDT R> Analog Input Value: [2: (13.19)]
09/12/01  2:53:47AM PDT R> Comm Status Report: [Total=1] [Airlink=

FIG. 11B

METHODS AND SYSTEMS FOR AUTOMATED PIPELINE TESTING

CROSS REFERENCE TO RELATED APPLICATIONS

This application is a continuation-in-part application of U.S. patent application Ser. No. 10/096,200, filed Mar. 12, 2002 now U.S. Pat. No. 6,822,432 issued Nov. 23, 2004, which claims the benefit of U.S. Provisional Application No. 60/300,348, filed Jun. 22, 2001, both of which are hereby incorporated by reference in their entirety.

BACKGROUND OF THE INVENTION

This invention relates generally to underground pipelines, and more specifically to maintenance and testing of underground pipelines.

Pipelines and other metallic structures inherently are subject to corrosion when placed underground. The corrosion process involves the removal of electrons or oxidation of the metal, and consumption of those electrons by some other reduction reaction, such as oxygen or water reduction. Corrosion is encouraged by the presence of moist soil in contact with a metal pipeline.

The electrochemical nature of the corrosion process provides opportunities to detect and mitigate corrosion of underground structures. Typical mitigation methods include applications of coatings to the structures and neutralizing the voltages and currents associated with the corrosion process through application of external voltages and currents.

Corrosion mitigation processes can be monitored to determine the extent of corrosion activity and to verify the effectiveness of electrical corrosion prevention systems. One known electrical corrosion prevention system for application of external voltages and currents to an underground structure, such as a pipeline, is referred to as a cathodic protection system. As part of the maintenance process, corrosion mitigation processes are monitored to determine the extent of corrosion activity. As a result, effectiveness of the cathodic protection system is also monitored.

The U.S. pipeline industry has standardized methods for assessing the performance of a cathodic protection rectifier system. One method used to detect corrosion activity and to assure the proper performance of the cathodic protection systems includes reading and verifying the output voltage of cathodic protection rectifiers, and reading and verifying the impressed current on the pipeline by measuring the voltage drop across a shunt resistor connected in series with the output of a cathodic protection rectifier. U.S. governmental regulations currently in place require measurement of rectifier voltage outputs at least once every two months.

Another conventional pipeline test, sometimes called an "on" potential measurement, includes reading the pipe-to-soil voltage at test points along the pipeline with cathodic protection rectifiers turned on, and verifying a potential between the structure and a reference electrode in the ground adjacent to the test point. One known U.S. testing standard requires verification of at least 850 mV between the structure and the reference electrode.

One proposed testing methodology includes reading a polarized voltage of the pipeline by reading the pipe-to-soil voltage at test points along the pipeline (typically located 100 yards to 1 mile apart) 100 msec to 1000 msec after all cathodic protection rectifiers affecting the test point have been simultaneously turned off. Such a test is sometimes referred to herein as an "instant off" potential measurement. The polarized voltage is a measurable potential between the structure and a reference electrode in the ground adjacent to the test point. Such a test would attempt to verify at least 100 mV between the pipeline structure and a reference point.

Another test, sometimes referred to as a close interval survey, involves measuring potential differences at very close intervals (around 3 feet) between the pipeline structure and adjacent soil both with cathodic protection rectifiers turned on as well as an instant after the rectifiers have been simultaneously turned off. Current close interval survey testing seeks to verify at least 100 mVolts of potential between the soil and the pipeline structure. However, conducting close interval surveys is a highly manual process, with a potential for errors, as described below. Therefore it is typical to only accomplish a close interval survey of about 20% of a pipeline in any given year.

When conducting close interval surveys, the current applied by all rectifiers affecting a particular segment of pipe are synchronously turned off and on (cycled) so that an applied voltage and a polarized voltage are recorded. Usually, survey crews are used to set up synchronized interruption equipment at each rectifier. The equipment initiates synchronized cycling and then the pipe to soil potentials are measured. Following the survey, the team returns to each rectifier location where synchronizing equipment has been temporarily installed to verify that the cycling activity occurred as expected and to remove the equipment for installation at a different pipeline segment. If the team cannot verify that the cycling activity was properly conducted at each rectifier location, the resulting collected data is rendered questionable and the survey may have to be repeated.

Underground pipelines may be adjacent to or near other structures which have ground contact and are therefore subject to corrosion. Cathodic protection systems sometimes are provided for such structures. The structure, as well as its protection system, may interfere electrically with the cathodic protection systems for the pipeline. The interference is typically manifested as undesired currents flowing between the pipeline and the structure. To control such currents, a shunt resistance may be placed between the structure and the pipeline. Such an installation is sometimes referred to as a critical bond. Testing of critical bonds is performed to ensure that the corrosion mitigation processes in place continue to be effective, and simply to verify that the current path between the structure and the pipeline has not been opened.

There is an increasing interest in checking the polarized voltage (or instant off potential) at pipe-to-soil test points as well as the constant potential at these sites. The polarized voltage tests supply pertinent pipeline corrosion data. Further, close interval surveys are becoming more common. However, the above described testing, as currently performed, is largely manual, and difficult to synchronize, utilizing known testing equipment.

BRIEF DESCRIPTION OF THE INVENTION

In one aspect, a method for testing operation of a cathodic protection rectifier (CPR) electrically coupled to a pipeline and a reference point is provided. The CPR is configured to apply a voltage to the pipeline and a cathodic system monitor which includes a cellular modem is configured to communicate with an external system and further configured to control and verify application of the voltage applied to the pipeline. The method comprises applying the CPR voltage to the pipeline through a shunt resistor, measuring the voltage across the shunt resistor with the cathodic system monitor, operating the cathodic system monitor to calculate a current applied to the pipeline by the CPR, transmitting the current calculations to the external system, and analyzing the current calculations utilizing the external system.

In another aspect, a system for monitoring a critical bond electrically connecting separate underground structures, the underground structures each including corrosion mitigation equipment applying a voltage to the respective structure is provided. The system comprises a shunt resistor electrically connected between the separate structures and a monitor configured to periodically measure the voltage across the shunt resistor. The monitor comprises a processor and a cellular modem interfaced to the processor. The monitor is further configured to transmit the measured voltages over at least one of a cellular control channel, a short messaging service cellular channel, and a general packet radio service.

In still another aspect, a method for monitoring a critical bond between separate underground structures, the underground structures each including corrosion mitigation equipment applying a voltage to the respective structure is provided. The method comprises electrically connecting a shunt resistor between the separate structures, and periodically measuring the voltage across the shunt resistor utilizing a monitor, the monitor configured to transmit the measured voltages over at least one of a cellular control channel, a short messaging service cellular channel, and a general packet radio service.

In yet another aspect, a method for monitoring operation of corrosion mitigation equipment applying an electrical voltage to a well casing is provided. The method comprises periodically measuring the voltage applied to the well casing with a monitor, and transmitting, to a site remote from the monitor, the measured voltage utilizing at least one of a cellular control channel, a short messaging service cellular channel, and a general packet radio service. The method further comprises receiving, at the remote site, the transmitted voltage measurement and determining, using the transmitted voltage measurement, whether the corrosion mitigation equipment is operational.

In another aspect, a test point monitor configured to monitor operation of corrosion mitigation devices for underground structures and structures having ground contact is provided. The monitor comprises a processor, a cellular modem interfaced to the processor, and at least one analog sensor interfaced to the processor. The monitor is configured with a wake-up cycle, and during the wake up cycle, the monitor is configured to cause a connection to be made to a testing point for the corrosion mitigation device and configured to measure at least one voltage utilizing the sensor. The monitor is also configured to transmit the at least one measured voltage utilizing the modem.

A method for adjusting an output of a cathodic protection rectifier is also provided. The cathodic protection rectifier is connected to a power source and configured to apply a voltage across the pipeline and a reference point in the soil, and a cathodic system monitor is coupled to the rectifier and further configured to control application of the voltage to the pipeline. The cathodic system monitor is configured to communicate with an external computer system. The method comprises receiving at the monitor, a communication from the external system to adjust an output of the rectifier, operating the monitor to adjust the output of the rectifier, operating the monitor to measure the adjusted output of the rectifier, and transmitting the measured output to the external computer system.

In another aspect, a cathodic protection rectifier system for an underground pipeline is provided. The pipeline is configured with a plurality of test points along a length of the pipeline, each electrically connected to the pipeline. The system comprises at least one cathodic rectifier coupled to a power source and configured to apply a voltage across the pipeline and a reference point in the soil, a cathodic system monitor coupled to the rectifier, the monitor configured to control the voltage the rectifier applies to the pipeline. The monitor is further configured to measure voltages and currents applied to the pipeline and to communicate the voltage and current measurements as pipeline test data. The system further comprises a computer system configured to receive the pipeline test data from the cathodic system monitor.

BRIEF DESCRIPTION OF THE DRAWINGS

FIGS. 11A and 11B are embodiments of pipeline monitoring data web pages.

DETAILED DESCRIPTION OF THE INVENTION

Figure 1:
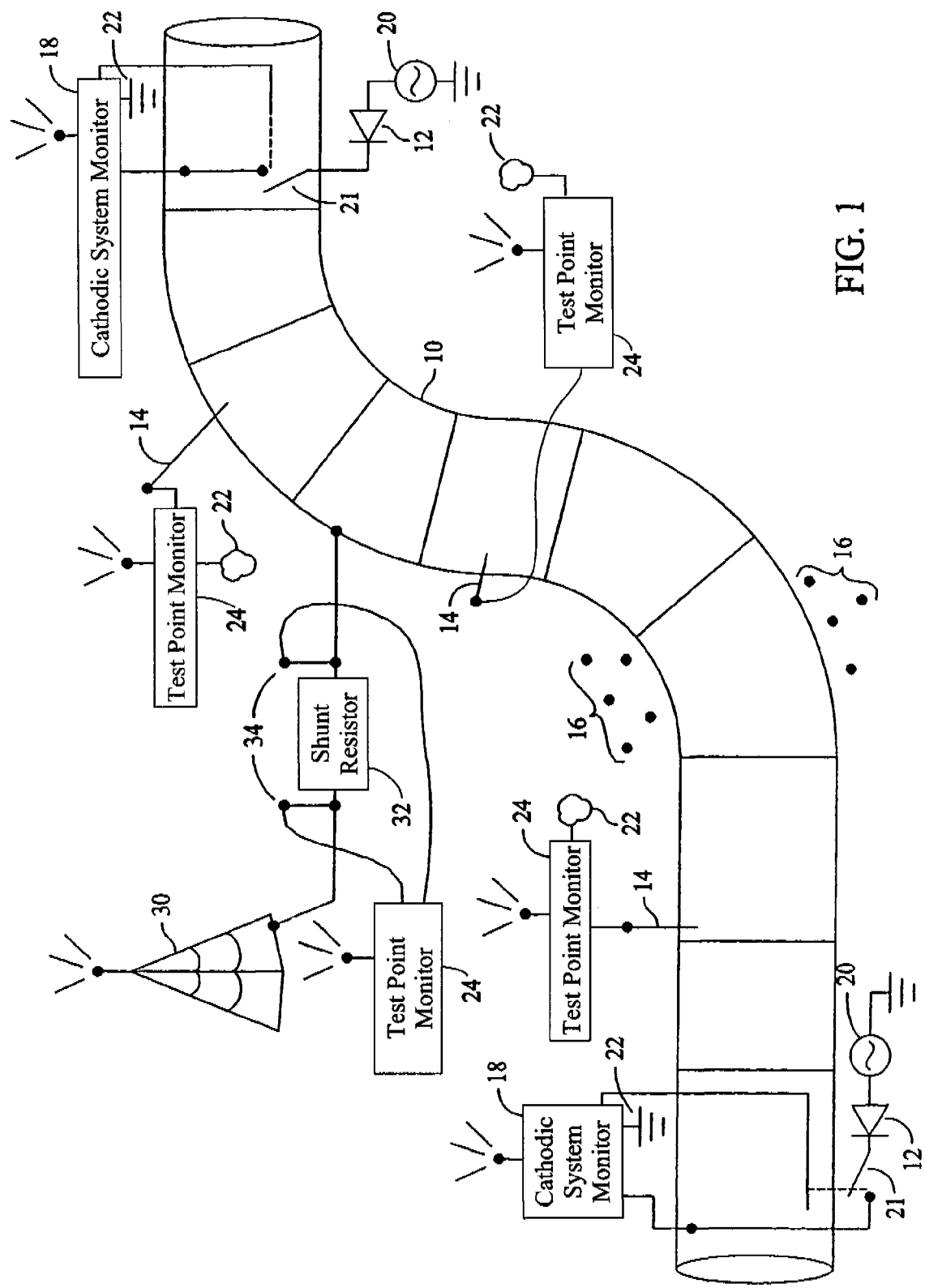
FIG. 1 is schematic illustration of a pipeline including cathodic protection systems, test points and close interval survey test points and incorporating various embodiments of pipeline remote monitoring units.

FIG. 1 is a schematic diagram of a pipeline 10 illustrating cathodic protection rectifiers 12, test points 14, and close interval survey test points 16. Cathodic system monitors 18 are utilized to measure, verify, and report output voltages and applied currents from cathodic protection rectifiers 12 on a pre-determined schedule, for example, once every two months. Cathodic system monitors 18 (described further in FIG. 2) are utilized to measure applied current, in one embodiment, by measuring a voltage drop across a low resistance value resistor (e.g. a shunt resistor (shown in FIG. 2)). Monitors 18 may also be configured to monitor power 20. In a particular embodiment, monitors 18 are configured to control switching devices, for example, relays 21 which switch the voltage output from cathodic protection rectifiers 12 to pipeline 10.

Known cathodic protection rectifiers are typically placed along a pipeline, for example, every three to five miles. The rectifiers are utilized to apply a voltage across an anode bed, or reference point 22 in the soil (electrical ground) and pipeline 10. The voltage applied is approximately equal to and oppositely polarized to a voltage that naturally occurs between the pipe and soil due to galvanic corrosion and is believed to minimize a rate of corrosion. Cathodic system monitors 18 facilitate cost effective testing of cathodic protection rectifiers 12 by measuring voltages and currents output by rectifiers 12 and delivering the measurement data to an external system. Cathodic system monitors 18 are also configurable, in one embodiment, for storing and archiving the measured voltage potentials measured across pipeline 10 and a reference point in the soil, and the current applied to the pipeline through the shunt resistor. In addition, power outages in power 20 are communicated along with any other alarm events through networks as described below. An alarm event includes, but is not limited to, an out of tolerance voltage supplied by cathodic protection rectifiers 12, as measured by monitors 18.

In one embodiment, test points 14 are spaced along pipeline 10 and are utilized when reading pipe-to-soil voltages induced by cathodic protection rectifiers 12. Test points 14 are electrically connected to pipeline 10 and provide an access point for making measurements along pipeline 10. Additional voltage measurements are made shortly after rectifiers 12 have been simultaneously disconnected from pipeline 10. The voltage measurements are used to ensure continued corrosion mitigation by cathodic protection rectifiers 12. The voltage test when rectifiers 12 are simultaneously disconnected is sometimes called a polarized voltage test or an "instant off" potential measurement. Test points 14 are located at various points along a pipeline, including, but not limited to, as close as 100 yards apart to as far as one mile apart. Measurements at test points 14 are made with respect to reference points 22, sometimes called an anode bed or buried reference cell, which are in the soil and spaced along pipeline 10. Test points 14 are electrically connected to the pipeline structure, for example, through a cable, and reference points 22 are typically reference electrodes in the ground near test points 14.

Testing which utilizes test points 14 in pipelines which contain multiple cathodic protection rectifiers 12 has heretofore been unreliable, labor intensive, and has required transportation and synchronization of discrete, temporary pieces of interruption equipment at each rectifier site. Monitors 18 are configured to notify operators, as described below, if cycling is not occurring at a rectifier site. Such notification during testing eliminates a possibility that testing will have to be redone after determining that a piece of interruption equipment at a rectifier site was not working during the tests, as is the case with known testing methods.

Close interval survey test points 16 are random points in the soil all along pipeline 10 and are utilized when measuring potential (voltage) differences between the pipeline structure and adjacent soil in an effort to determine if pipeline coatings have separated and pipeline 10 has become exposed to the soil. In one close interval survey test the voltage at test points 16 are measured with all cathodic protection rectifiers 12 simultaneously connected to pipeline 10 (sometimes called a constant potential test). Another test includes synchronously switching relays 21 (cycling) to disconnect cathodic protection rectifiers 12 from pipeline 10 and measuring the voltage potentials at test points 16 in an "instant off" test, as described above. Monitors 18 are configured to notify operators if a rectifier 12 is not operating properly, ensuring reliability in the data collected in a close interval survey.

Figure 2:
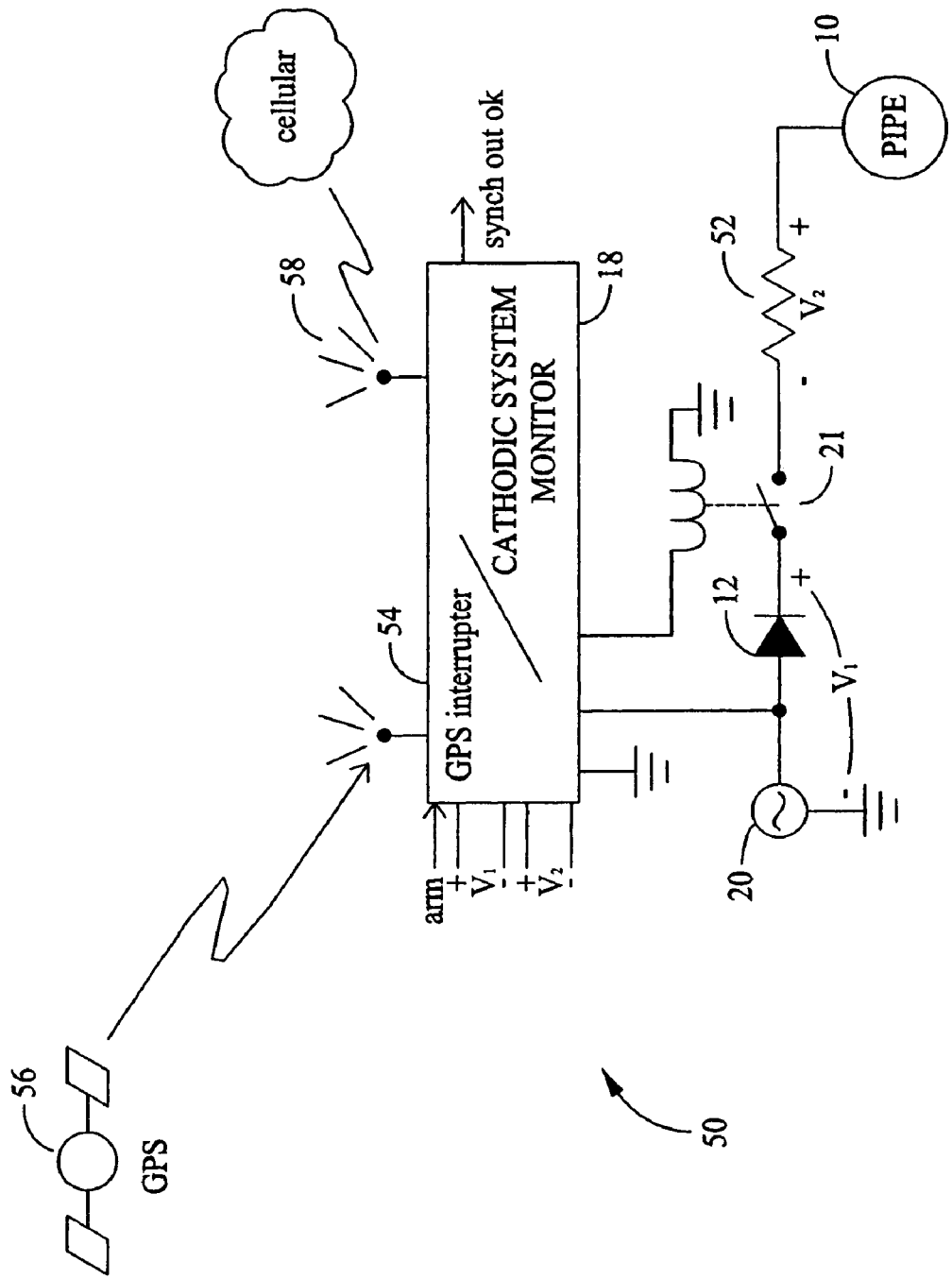
FIG. 2 is a schematic diagram of a cathodic protection system.

As described above, cathodic system monitors 18 are configured to measure and verify output voltages of rectifiers 12 and further to measure and verify current applied by rectifiers 12 using a shunt resistor (described in FIG. 2). In addition, cathodic system monitors 18, in one embodiment and as described below, are configured to emulate cellular phone communications techniques. Cathodic system monitors 18 also include provisions for accessing networks to allow a high level of monitoring and testing performance, both functionally and economically, as compared to known testing and monitoring methods. Utilization of cathodic system monitors 18 allows data affirming proper operation of cathodic protection rectifiers 12, for example, voltage potentials between the pipe and soil, to be periodically collected, stored, delivered, and archived for analysis.

In addition, power outages or out of tolerance corrosion mitigation voltages supplied by rectifiers 12 may be communicated along with other alarm events through an existing cellular network, as further described below. The cellular communications are possible as monitor 18 emulates cellular phones in order to transmit data, for example, voltages and currents, using the cellular network. The data is sent through a data gateway where it may be displayed on an Internet web site or sent secondarily to end users over email, fax, and pager links, enabling users to monitor and verify operation of monitors 18.

Pipeline 10 is further configured with, in the embodiment shown, a number of test point monitors 24, which are powered by one or more of battery and solar power. Test point monitors 24 are typically installed at test points 14 where utility power is not available. Test point monitors 24 may be configured to include most of the functionality of monitors 18 as described above. Test point monitors 24 also include the cellular communications capabilities described above. Test point monitors 24 may be configured by the user to power up at programmable intervals to perform tests including, but not limited to, collecting pipe-to-soil voltage readings, verifying proper pipe-to-soil potentials, and sensing synchronized interruption activity (switching of relays 21) on the pipeline for the purpose of taking synchronized pipe-to-soil potential readings. In addition, both monitors 18 and test point monitors 24 can perform a number of other valuable functions such as reading, storing, and archiving readings on a prescribed schedule (without transmitting readings). Further, monitors 18 and test point monitors 24 are configured for analyzing the archived readings and transmitting statistical information about the collected values such as maximum, minimum, and average values. Monitors 18 and 24 are also able to determine whether forwarded channel information is pending in a server queue for polling or modifying operating parameters of monitors 18 and test point monitors 24 via the cellular network.

As the measurements taken by test point monitors 24 are periodic, with long periods of non-activity between testing cycles, test point monitors 24 are configured with sleep modes for conservation of battery resources. In one embodiment, described in further detail below, test point monitors 24 are configured to periodically "wake up" and determine if synchronized interruption activity is present on pipeline 10, as measured at test points 14. During this wake up cycle, test point monitor 24 measures the pipe-to-soil potential, and determines whether the source of potential (rectifiers 12) is being switched on and off (e.g. cycling) at regular intervals. The switching intervals are controlled by monitors 18 utilizing relays 21 as described above. In one specific embodiment, the switching interval is between once per second and once every 10 seconds. In this configuration, the switching interval, or cycling, of the voltage applied to pipeline 10 is implemented by cathodic system monitor 18 commanding, for example, a GPS precision interrupter (shown in FIG. 2). Pipeline 10, therefore acts as a communication media, for signaling test point monitor 24 that such readings are being requested.

Another test which can be implemented using test point monitors 24 is critical bond testing. Sometimes underground pipelines 10 are adjacent to or near other structures 30, for example radio towers or other pipelines, which have ground contact and are therefore subject to corrosion. To protect pipeline 10 and structure 30 from interfering with one another due to natural currents occurring between the two, pipeline 10 and structure 30 are electrically connected through a shunt resistance 32 placed between structure 30 and pipeline 10. Such an installation is sometimes referred to as a critical bond. Testing of critical bonds using test point monitor 24 is accomplished by measuring a voltage across shunt resistance 32 through use of shunt test points 34. Measuring the voltage across shunt resistance 32 allows operators to determine if the electrical connection between pipeline and structure 30 is intact and operating within specifications.

Physical mounting of cathodic system monitors 18 and test point monitors 24 near pipeline 10 may be accomplished using a variety of configurations. Electrically, monitors 18 are connected to both pipeline 10 (for example, at an output of rectifier 12) and to a reference point 22 in close proximity. Test point monitors 24 are connected to both pipeline 10 (for example, at a test point 14) and to a reference point 22 near the test point. Monitors 18 are typically mounted in an enclosure which includes rectifier 12. Monitors 24 may be mounted to a riser using a metal bracket. Alternatively, test point monitors 24 may be mounted at soil surface level, attached to a buried cylindrical tube also housing reference point 22. Further, test point monitors 24 may be mounted to any structure adjacent to pipeline 10 where electrical connection may be established to test points 14 and reference points 22.

FIG. 2 is a schematic diagram of a cathodic protection system 50. Power 20 is rectified for application to pipeline 10 using rectifier 12. The output of rectifier 12 is switched to pipeline 10 through a relay 21. In series between relay 21 and pipeline 10 is a shunt resistor 52. In addition to measuring the voltage output (V1) of rectifier 12, cathodic system monitor 18 is configured to measure a voltage (V2) across shunt resistor 52. Since a resistance value of shunt resistor 52 is known, measuring the voltage across shunt resistor 52 allows monitor 18 to determine a value of current applied to pipeline 10. In an alternative embodiment, a hall effect device (not shown) is used to measure applied current. As monitor 18 is configured to control relay 21, monitor 18 is able to implement synchronous switching, or cycling of the rectifier voltage, as described above.

In one embodiment, monitor 18 is configured with pre-programmed switching intervals, including, but not limited to, a start time, a stop time, an "on" period, and an "off" period. The pre-programmed switching intervals allow implementation of the synchronous testing described above. However, pipeline 10 (also shown in FIG. 1) is typically outfitted with multiple rectifiers 12 each controlled by a monitor 18. To ensure synchronicity when switching a number of rectifiers 12, monitors 18 are configured with GPS interruption circuitry 54. In an alternative embodiment, GPS interrupter 54 is physically separate from monitor 18. GPS interrupter 54 communicates with a GPS satellite 56, and therefore provides a timing mechanism which ensures that all monitors 18 (GPS interrupters 54) are programmed with an equivalent real clock time. With an equivalent real clock time, and pre-programmed switching intervals, monitors 18 are able to control synchronous application of voltages to pipeline 10 and synchronous removal of voltages from pipeline 10. In one embodiment, monitors 18 receive a "synchronization OK" signal from GPS interrupter 54, based upon received pipeline voltage and/or current measurements as compared to an applied switching interval. Through the cellular interface described below, operators can verify the pipeline testing sequence is valid (i.e. all rectifiers are being switched off and on as desired).

In one embodiment, cathodic system monitors 18 and test point monitors 24 (shown in FIG. 1) are dedicated to the task of automating collection and analysis of pipe-to-soil potentials. Monitors 18 and 24 are further configured to communicate over a cellular control channel 58 and incorporate control channel messaging as a wireless link to the end-user. In the embodiment, for example, start time, stop time, "on" period, and "off" period information is downloaded into monitors 18 over control channel 58. In such an embodiment, all communications from cathodic system monitors 18 and test point monitors 24 are in a digital format, ensuring reliable communications in areas where voice cellular coverage is marginal. In another embodiment, monitors 18 provide an arming signal to GPS interrupter 54 which initiates testing. Cellular control channel communications are desirable since only small amounts of alarm, status, and survey information need to be transported in pipeline monitoring and surveying applications. Other communications types, for example, private radio or switched telephone, cellular or landline, have been found to be cost prohibitive due to ongoing operational costs.

Figure 3:
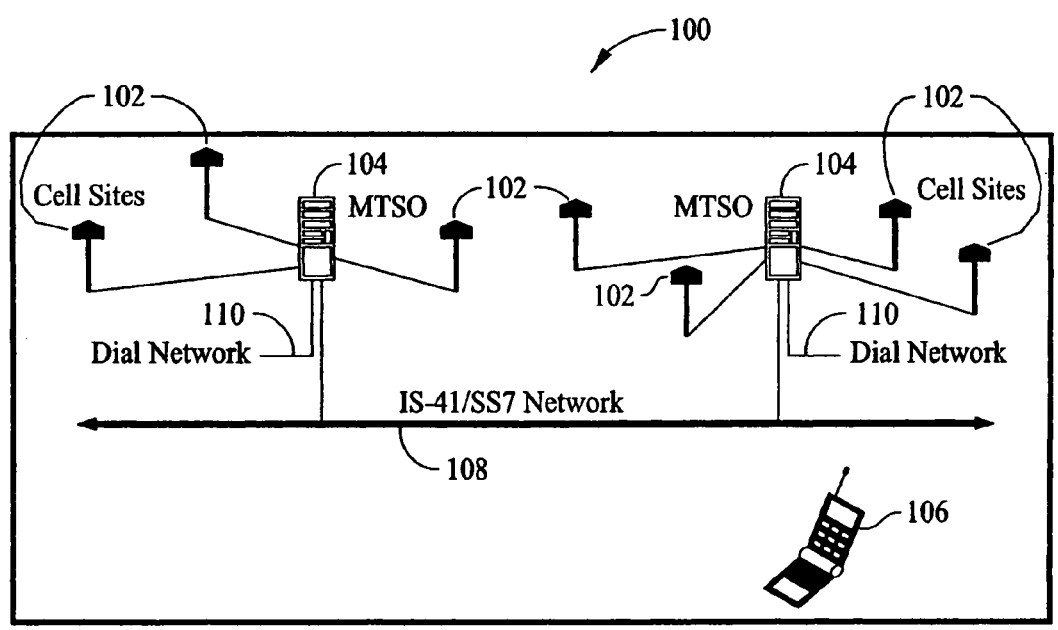
FIG. 3 is a diagram of a cellular telephone network.

Cellular control channel communications use an underutilized component of existing cellular telephone networks. A schematic diagram of such a network 100 is shown in FIG. 3. Network 100 typically includes multiple cell sites 102 or towers, a plurality of which are communicatively coupled to a mobile telephone switching office (MTSO) 104. Typical cellular networks, similar to network 100, may include multiple MTSOs 104, each communicating with multiple towers 102. Cell sites 102 transmit and receive signals to and from the individual cellular telephones 106 within a service area of the cell sites 102. The number of cell sites 102 per MTSO 104 varies according to geography and other factors. Each MTSO 104 is configured to interface to a network 108. Network 108 is, in one embodiment, an IS-41/SS7 network. Each MTSO 104 further interfaces to a local dial network 110.

Control channel communication is optimized for the transport of small packets of information over vast geographic areas at an extremely low cost. Advantages of control channel communication include that such communications utilize an existing network, utilizing proven technology, accessible in even the most remote areas. In addition, there are no capital equipment outlays necessary to establish the wide area network, no cellular telephone dialing occurs, so there are no monthly telephone line or cellular fees. Also there is no ongoing support or maintenance costs to support the wide area network.

In known cellular networks, each cellular provider uses a dedicated set, in one embodiment, about five percent, of their assigned channels as control channels. These channels are digital and are not used for voice conversations. Rather, the control channels are used solely for communicating administrative information to and from the cellular telephones in a service territory.

One known control channel communication protocol requires that each message be duplicated 5 times during each 125 msec transmission sequence, and that 3 out of 5 messages be identical for acceptance. Information delivered using the cellular control channels is also transmitted at a proportionally higher power than voice channels. During voice conversations, the cell site through which a cellular telephone is communicating is instructing the cellular telephone to reduce its power to the minimum necessary to achieve communications with that cell. The reduction in power allows reuse of the frequency at other cell sites. However, control channel power is not reduced, assuring geographical coverage even in areas where voice coverage is marginal.

Figure 4:
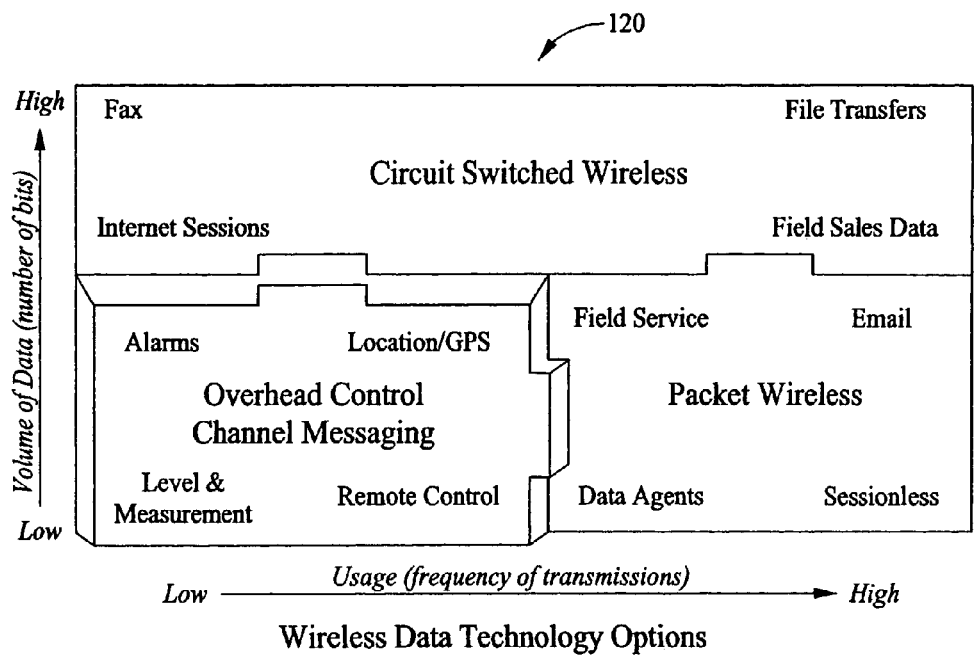
FIG. 4 is a graph comparing communication types by volume of data against frequency of cellular transmissions.

While a particular cell system may be saturated with voice calls, the control channels are still relatively available, and each one is able to process 36,000 message packets per hour. FIG. 4 is a graph 120 charting communication types by volume of data against frequency of transmissions. Chart 120 shows that control channel communications are effective for low volumes of data and relativity low update rates.

Even at the busiest times, control channels are operated at less than 25% capacity. The control channels provide many pieces of information to and from cellular telephones, using a forward channel and a reverse channel. Information is sent over forward control channels (FOCC) to instruct cellular telephones how to operate in a given service territory, identify the local system, and initiate the ringing, or paging, of cellular telephones. Reverse control channels (RECC) send dial requests and ring responses from the cellular telephones to the system along with roaming registration requests. Two functions performed by the control channels used by cellular cathodic system monitors 18 and test point monitors 24 are RECC Roaming Registration and FOCC Paging.

RECC Roaming Registration

Figure 5:
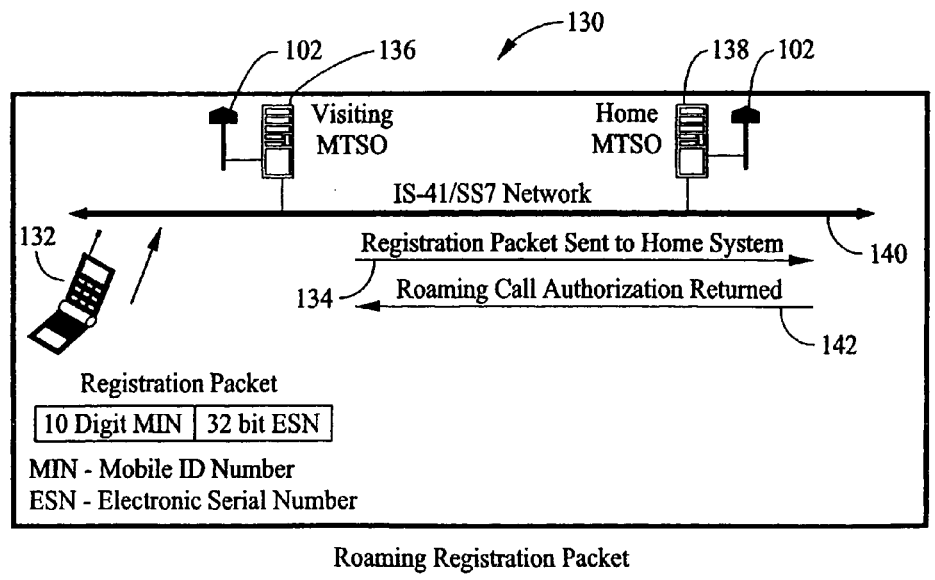
FIG. 5 is a schematic diagram of a roaming registration system for cellular telephones.

When a cellular telephone enters a non-home area, forward channel information from the nearest cell site identifies what system the phone has entered, using a System ID (SID). FIG. 5 is a diagram 130 showing roaming registration for a cellular telephone 132. Cellular telephone 132 is programmed with a home SID, and when telephone 132 recognizes that it is in a non-home area, telephone 132 automatically attempts to register itself for use in that service territory by sending a roaming registration packet 134 comprised of two pieces of information—a MIN (Mobile Identification Number) and an ESN (Electronic Serial Number) for the telephone. The MIN is the 10 digit telephone number of cellular telephone 132, and the ESN of telephone 132 is established at the time of cellular telephone manufacture.

Roaming registration packet 134 is received by the local cell at a visiting MTSO 136, which looks at the MIN to determine an SID of cellular telephone 132. MTSO 136 then instantly routes that registration packet back to the home MTSO 138, based upon received SID, over IS-41 network 140. Home mobile telephone switching office (MTSO) 138 is configured to look up account information and sends back a message 142 over IS-41 network 140 telling visiting MTSO 136 whether or not calls to be placed from cellular telephone 132 in that service territory (MTSO 136) should be allowed. Data exchange for packet 140 and message 142, takes less than ten seconds.

FOCC Paging

When a call is placed to a cellular telephone, the system sends out what is referred to as a page, the MIN or telephone number of the cellular telephone, over a Forward Control Channel (FOCC). If the call is answered by the cellular telephone, a page response is sent back and a voice channel is then assigned so that the conversation sequence may commence. Once on a voice channel the conversation never uses the control channels again. Cell and channel hand-offs are accomplished over the voice link, keeping the control channel free to process call initiation functions.

RECC Dial Feature Code Requests

The cellular network allows special features, for instance allowing users to enter instructions into the system that cause calls placed to an unanswered cellular telephone to be re-directed to another number. These dial features are entered using number sequences such as *70 314 555 1212, where the *70 is interpreted as an instruction and the number that follows (314 555 1212) as the telephone number to be dialed if the cellular telephone does not answer in a given number of ring cycles.

To establish this feature, the complete set of digits are "dialed" by sending the digit string over the cellular control channels. When received by a cellular base station, the digit string is processed by the switch and a call-vectoring setup is accomplished. The RECC feature code request is one process used for data transport from a remote device, for example, cathodic system monitors 18 and test point monitors 24, across the cellular network, and back into a server for user access.

Use of Control Channels for Third-Party Messaging

By emulating the FOCC and RECC functions, third party information packets may be sent through existing cellular networks, allowing communication of data to occur virtually anywhere. As described below, a gateway is provided through which these information packets, also referred to as datagrams, are routed outside the cellular telephone network, to client-side information servers.

In one embodiment, cathodic system monitors 18 and test point monitors 24 include an embedded functional equivalent of a cellular telephone without keyboard, display, and audio circuitry. When voltage readings or alarm and status data are to be sent, a remote monitor, for example, cathodic system monitors 18 and test point monitors 24, transmit a packet of information to the closest cellular telephone tower 102 (shown in FIG. 3). This information packet looks exactly like an RECC registration packet to the existing cellular system. In the MIN field is the monitor's telephone number, one of several million numbers that are not used by wireless cellular, paging, or wireline services. In the electronic serial number (ESN) field of the registration packet are the voltage readings and alarm and status information. This information is received by the cellular network at the closest tower in the same way that a roamer registration request packet is received. However, instead of routing the packet to a distant home SID, the cellular network routes the voltage readings and alarm and status information through a gateway to at least one computer, in one embodiment a server, where it is placed into a portion of a database reserved for use and access by a particular client. The same information flow results over the cellular network regardless of whether the technology employed are RECC Dial Feature Code Requests or RECC Roaming Registration Requests.

Using the above described wireless wide area cellular network, alarm, status, and survey data from pipelines are reliably delivered from remote locations and, in one embodiment, directly into an Internet Web Page. Other client-side delivery methods are also available including automated e-mail, facsimile, pager, telnet, and Private Virtual Circuit (PVC) Frame Relay links into existing Intranet applications. In one embodiment, costs for delivery of voltage measurements, and alarm and status data are transaction-based and involve no monthly telephone line charges or cellular access fees. Therefore pipeline monitoring and surveying applications that have not been able to economically justify conventional communications techniques are brought on line and are fully accessible, for example, over the Internet.

Figure 6:
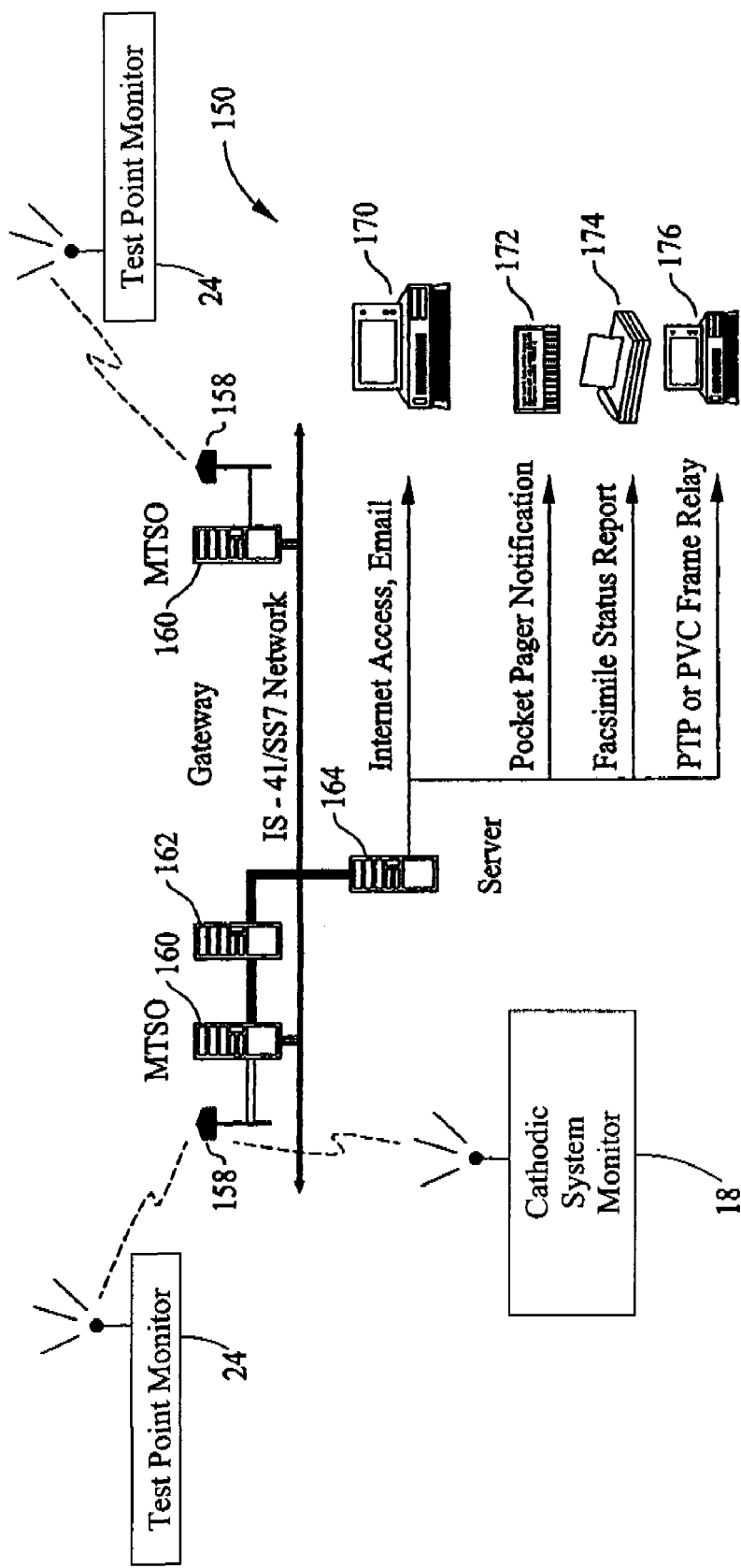
FIG. 6 is a schematic diagram of a control channel communication based pipeline monitoring system.

FIG. 6 is a diagram of a control channel communication based pipeline monitoring system 150. System 150 includes at least one of cathodic system monitors 18 and test point monitors 24 (shown in FIG. 1). Any number of cathodic system monitors 18 and test point monitors 24 arrangements are possible at pipeline 10. In one embodiment, cathodic system monitors 18 and test point monitors 24 are configured for monitoring and testing sections of pipelines, as shown in FIG. 1. In such an embodiment, cathodic system monitors 18 and test point monitors 24 are configured to periodically transmit data packets which include voltage measurements, for example, "On" potential and "instant off" potential measurements which relate to the functionality of cathodic rectifiers and pipeline protection practices, and any other pertinent information, in a digital format, to cellular tower 158. Voltage readings and other data received at tower 158 are propagated to mobile telephone switching office (MTSO) 160, where, based upon identification information contained within the data packets, the voltage readings and other data are transferred via a gateway 162 to server 164, in one embodiment, via the Internet.

Pipeline companies and companies contracted to the pipeline companies or a governmental agency, are able to access the information received from cathodic system monitors 18 and test point monitors 24 via any one of Internet access/E-mail 170, pocket pager 172 notification, facsimile 174, and PTP or private virtual circuit (PVC) frame relay 176. As shown in FIG. 6, multiple cathodic system monitors 18 and test point monitors 24, are able to transmit data packets to towers 158, thereby providing a railroad or governmental agency with an ability to data track and log the multiple test points along a pipeline using testing methodologies as described above. In certain embodiments, information is received from cathodic system monitors 18 and test point monitors 24 at a centralized database and data center.

Figure 7:
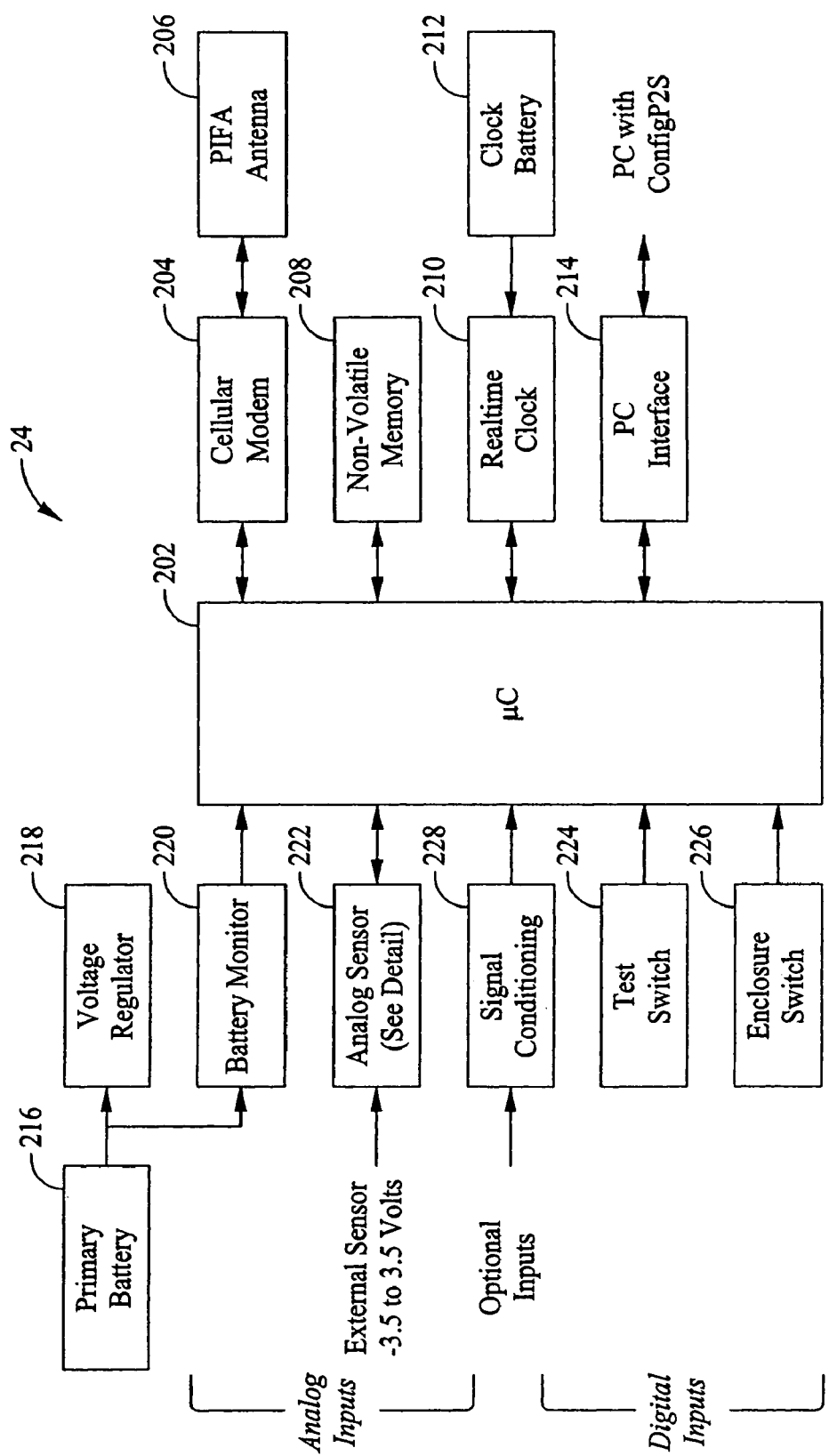
FIG. 7 is a schematic block diagram of a test point monitoring unit.

FIG. 7 is a schematic block diagram of a test point monitor 24. Test point monitor 24 includes a microcontroller 202 to which is connected a cellular modem 204 and an antenna 206, enabling the cellular control channel communications as herein described. Test point monitor 24 also includes a non-volatile memory 208, which has operating instructions for micro-controller 202 loaded therein, a real-time clock 210 and clock battery 212, and a computer interface 214 for communications with a computer to enable downloading of updated pipeline testing frequencies or testing sequences, for example.

Test point monitor 24 further includes a primary battery 216 which is connected to a voltage regulator 218 and a battery monitor 220, which is configured as an input to micro-controller 202. Other inputs to micro-controller 202 include analog sensors 222, a test switch sensor 224, an enclosure switch sensor 226, and optional signal conditioning circuits 228.

Test point monitor 24 is a low power device configured for periodic collection of pipe-to-soil voltages through the same cellular-based system used for communications with cathodic system monitors 18. To conserve power, test point monitors 24 are configured with wake-up cycles. The wake-up cycles, in one embodiment, are set at pre-programmed intervals, where test point monitor 24 powers up and checks for a cycling voltage which is being transmitted along the pipe. The cycling voltage instructs test point monitor 24 to begin performing one or more tests, typically the synchronous interruption ("instant off") tests as above described, and typically at a time during the on-off cycles that is pre-programmed into test point monitor 24. If no voltage cycling is present, or if testing is complete, test point monitor 24 powers down to a sleep mode, until the next preprogrammed power up cycle time. In another embodiment, wake-up cycles and times for measurements are transmitted directly to test point monitors 24 over the cellular control channel during a wake-up cycle.

Figure 8:
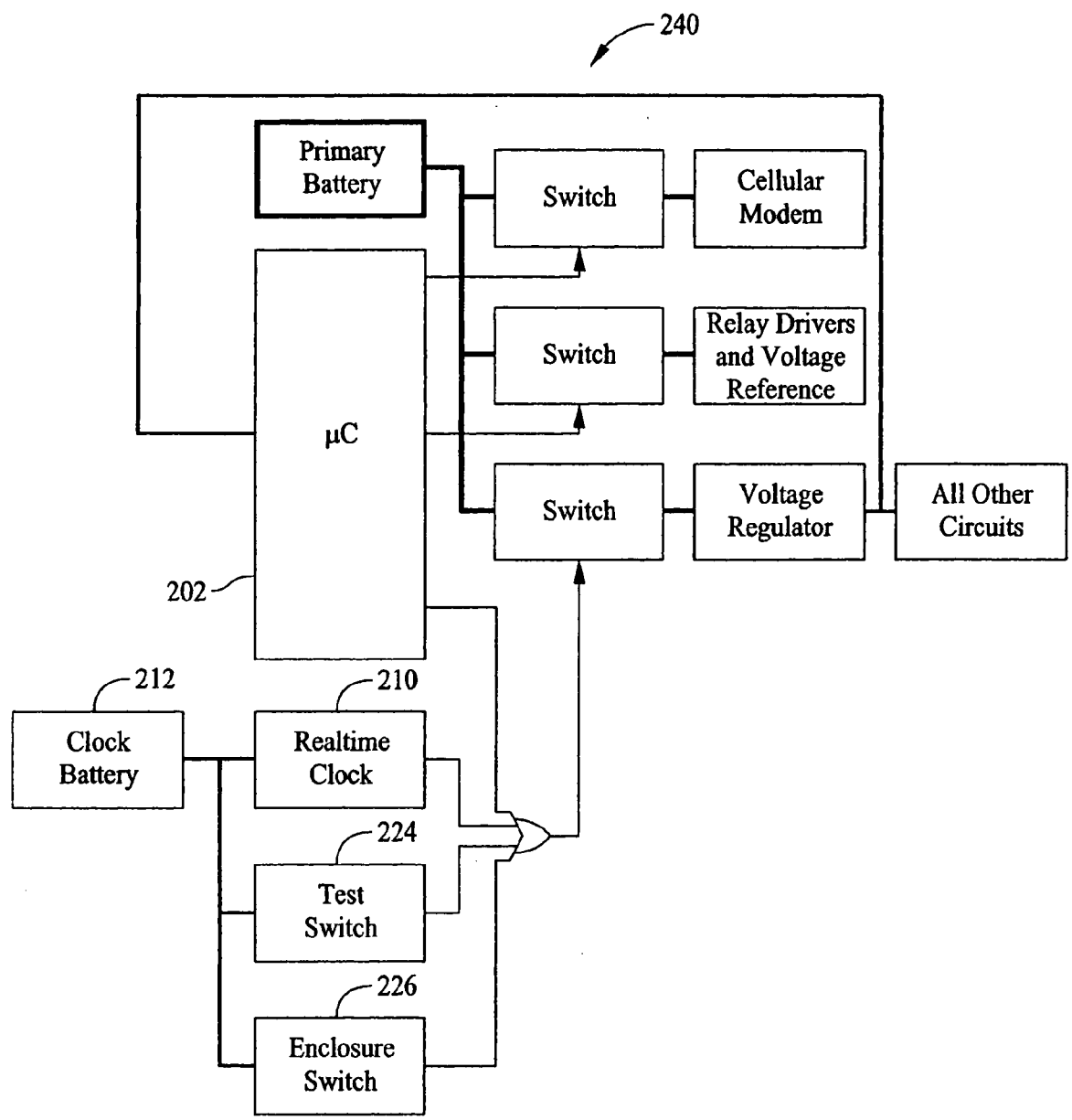
FIG. 8 is a schematic block diagram showing real-time clock functions for the test point monitoring unit shown in FIG. 7.

FIG. 8 is a schematic block diagram 240 illustrating how the above described wake-up cycles are managed within test point monitor 24. Real time clock 210, separately powered by a battery 212, is configured by microprocessor 202 to initiate a wake up at a particular date and time. Alternately, an internal tamper detection switch (enclosure switch 226) or test switch 224 may also initiate wake-up activity—in the first instance to report potential tampering with the device and in the second to execute an internal test procedure to verify correct device operation.

Once test point monitor 24 is powered-up, that is, a wake-up cycle initiated, microprocessor 202 takes control, and determines and executes the activities to be conducted during the wake-up cycle, schedules the next wake-up cycle, and causes the unit to power back down into a dormant state, with only real-time clock 210 running in preparation for the next wake-up cycle.

In addition, power outages or other alarm events along pipeline 10 are communicated through cellular network 100 (shown in FIG. 3) and secondarily to end users over email, fax, and pager links during wake-up cycles. To wake-up test point monitors 24, to begin an instant off measurement cycle, commands are delivered to monitors 18, as described above over the cellular network or other means, which are deployed over wide geographic territories, instructing monitors 18 to begin a preprogrammed synchronous interruption cycling, using GPS-derived timing, transmitted to and from GPS interrupter 54. By obtaining synchronization using commonly available GPS as a time base, asynchronous activation of devices over a relatively slow and non-synchronized cellular communication link ultimately establishes a very tightly controlled process. The process includes simultaneous rectifier on-off cycling of cathodic protection rectifiers 12, which is necessary for timing synchronized instant off readings from test points 14, thereby eliminating an error prone manual process. Further, a synchronization system incorporating cathodic system monitors 18 is activated, and in one embodiment, can verify that high current levels are, in fact, being properly controlled, through a feedback process, allowing the user to verify proper coordinated cycling before the time and expense of actual close interval data collection.

Test point monitors 24 are configurable for a variety of functions, including, but not limited to, log voltages then sleep, send voltages then sleep, check for communications, reading voltages, do not send voltages until an alarm is turned on, analyze stored readings, send statistical information, check for oscillations and turn on/off cathodic protection systems.

Figure 9:
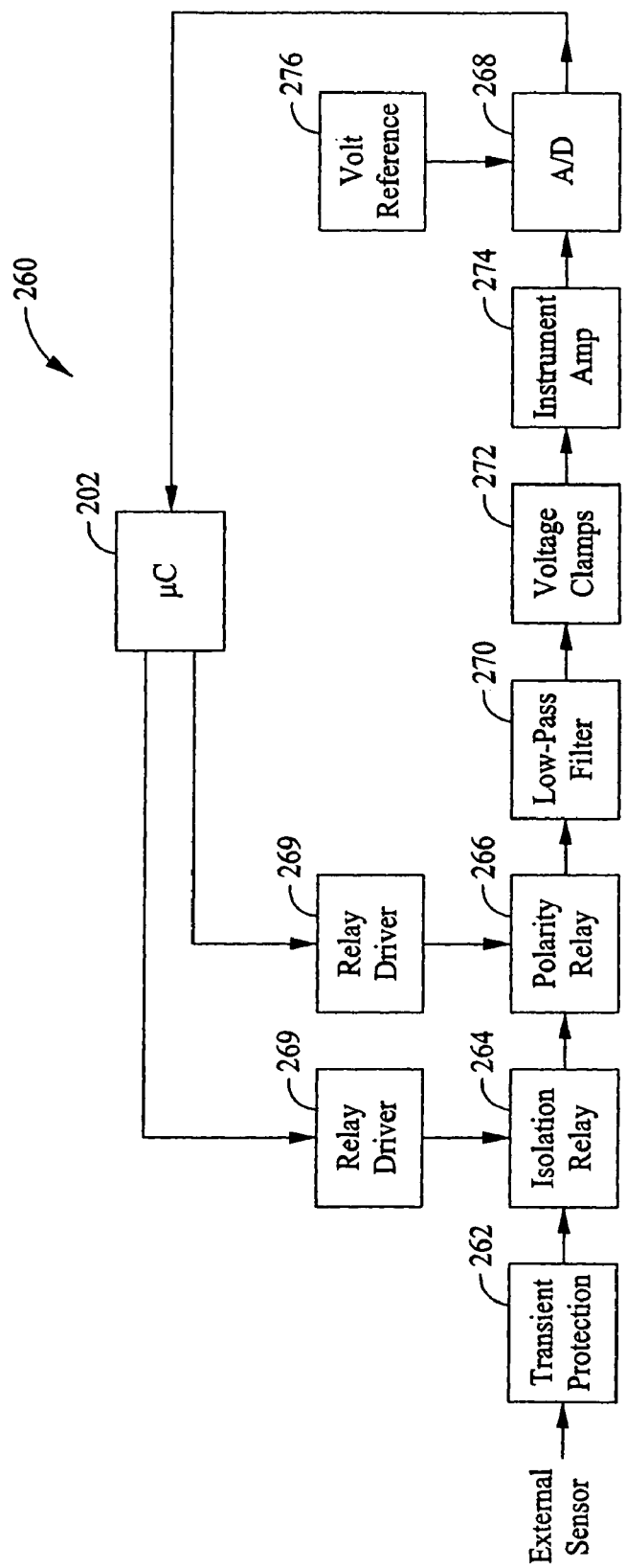
FIG. 9 is a functional block diagram for the test point monitoring unit shown in FIG. 7.

FIG. 9 is a schematic block diagram of an analog input monitoring channel 260 illustrating circuitry through which test point monitors 24 perform pipe-to-soil voltage testing. It is important to collect accurate readings from test points, and to filter out other induced voltages that may manifest as voltage offset errors. Analog input monitoring channel 260 is configured with a high input impedance to prevent affecting the polarization of the test point and measurement of the very low signal level. The voltage reading is taken between the pipeline test points 14 (shown in FIG. 1) itself and buried reference cells 22 (shown in FIG. 1) which are in close proximity to pipeline 10 (shown in FIG. 1). Typically, reference cells 22 enhance conductivity with the soil and impose a DC voltage offset that is factored out of the reading taken by at the test points. Analog input monitoring channel 260 also provides transient protection 262.

Test point monitors 24 contain an isolation relay 264 that provides isolation from test points 14. Isolation relay 264 delivers an infinite input impedance except for those very brief time periods, in one embodiment less than 1 second, when readings are actually being taken, as instructed by microcontroller 202 (also shown in FIG. 8). Following isolation relay 264 is a polarity relay 266 used by microcontroller 202 to establish positive or negative polarity—allowing a single ended analog to digital converter 268 to be used in a bipolar environment. Microcontroller 202 is configured to control opening and closing of relays 264 and 266 through use of relay drivers 269.

A low pass filter 270 eliminates rectified RF noise from high frequency sources and high noise sources, for example, nearby light rail trains and a voltage clamp 272 and an instrumentation amp 274 further cleans the signal from the test point, for measurement by A/D converter 268, which compares the signal to a reference 276. Finally, under direction of microprocessor 202, and in one specific embodiment, between 512 and 1024 readings are taken and averaged at a multiple of 16.67 millisecond and 2.50 millisecond intervals to eliminate the effect of inductively coupled noise signals, for example, from 60 Hz overhead power lines and 400 Hz power transmission sources.

By using the synchronized interruption process, cathodic system monitors 18 and test point monitors 24 are able to read, average, and deliver "instant off" potential readings, without the manual placement of synchronization instruments, as in the known manual process. In such a configuration, rectifier current cycling of cathodic protection rectifiers 12 under control of monitors 18, and the pipeline itself act as a command and communication media for signaling test point monitors 24 that such a reading is being requested.

Using available overhead control channels of the cellular telephone network, a battery-powered or solar powered test point monitor, for example, test point monitor 24, can read and transport pipe-to-soil voltage readings, and other pipeline test data, that are presently collected on a manual basis involving travel to each remote site. In addition, test point monitors 24 can determine when alarm conditions have developed, such as out of tolerance of pipe-to-soil potentials, and alert users to these conditions. Also, and as described above, test point monitors 24 can detect when synchronized interruption is occurring, take a particular reading during the interruption, and forward this reading to a centralized location. By providing the cellular communications whereby this information can be delivered into a centralized database, users can retrieve pipe-to-soil potential data over the Internet, or it may be forwarded through techniques such as email, facsimile, pocket pager or other data networking connections.

Figure 10:
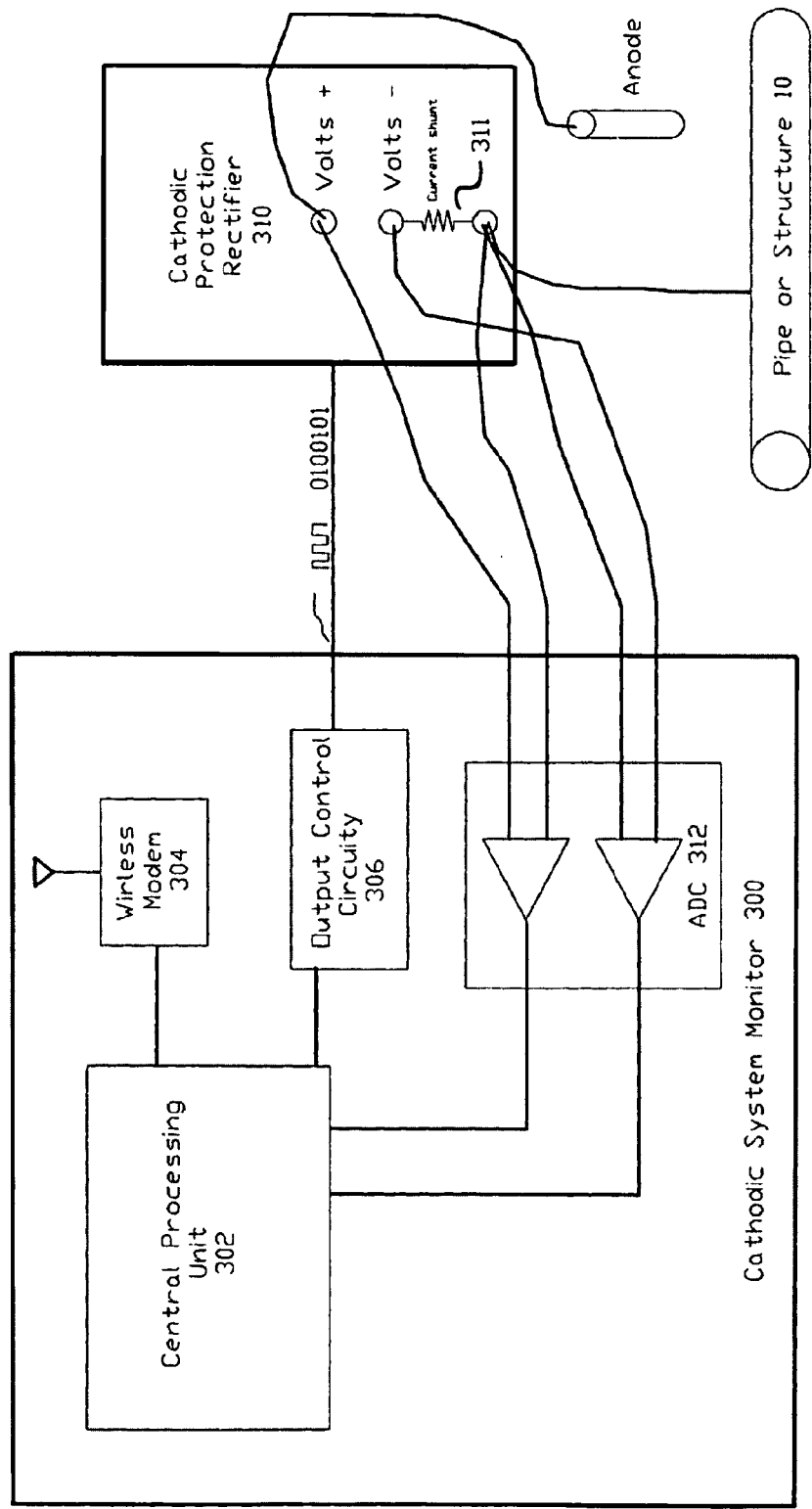
FIG. 10 is a functional block diagram of a cathodic system monitor.

FIG. 10 is a functional block diagram of an alternative embodiment of a cathodic system monitor 300. Cathodic system monitor 300 include a central processing unit 302, a wireless modem (cellular or other type of wireless device) 304, and output control circuitry 306. In the embodiment, communications received at wireless modem 304 are interpreted by central processing unit 302, which outputs commands to output control circuitry 306. The commands result in changes to the output of output control circuitry 306 such that output control circuitry 306 is utilized to regulate an amount of voltage that is applied to pipeline 10 by rectifier 310. In one embodiment, commands from central processing unit 302 resulting in a full-scale output of output control circuitry 306 corresponds to a full-scale voltage output by rectifier 310.

In operation, communications are received via wireless modem 304 using cellular analog control channel (other embodiments include, but are not limited to, cdma, gprs, and other types of wireless devices). The communications are interpreted by central processing unit 302, which provides the communicated output control, via output control circuitry 306. One example of output control circuitry 306 is a microcontroller having an on board digital-to-analog converter (DAC). In such embodiments, central processing unit 302 and output control circuitry 306 are incorporated as a single unit. Another example is an external DAC. As described above, voltage controlled rectifier 310 applies a voltage and current to pipeline 10, in one embodiment, through shunt 311. Voltage controlled rectifier 310, includes several alternative embodiments, including, but not limited to voltage rectifiers, pulse width modulation, digital potentiometers, and digitally controlled rectifiers. Of course with these different embodiments for rectifier 310, different embodiments exist for output control circuitry 306, so that the two are compatible for communications.

After setting the output of output control circuitry 306 (a voltage, a signal or a digital command), and applying the output to rectifier 310, cathodic system monitor 300 is then utilized to measure the voltage and current applied to pipeline 10. In the embodiment illustrated, voltage and current applied to pipeline 10 are measured utilizing an analog to digital converter (ADC) 312. In alternative embodiments, ADC 312 is one of and external DAC or an on board DAC within a microcontroller, similar to the DAC described above. In the above described embodiments, the voltage and current measurements are sent back to a user or another external system utilizing wireless modem 304.

In a numerical example, if the maximum voltage able to be output by rectifier 310 is ten volts and the maximum DAC output voltage from output control circuitry 306 is five volts, an instruction setting the output of the DAC within output control circuitry 306 to one volt results in two volts being applied by rectifier 310 to pipeline 10.

FIGS. 11A and 11B are two embodiments of web pages where a user can access pipeline test data. Regardless of which the above described wireless technologies are used, the network servers provide routing nodes for information passing to and from monitors 18 and test point monitors 24. Networks typically utilize the Internet as a means of user access, not only for communication with monitors 18 and test point monitors 24, but for establishing and administrating users, configuring network behavior, and managing real-time and historical data. The web pages in FIGS. 11A and 11B are two examples of web pages that are used to gather data from, and change operating and testing parameters for one or more of cathodic system monitors 18 and test point monitors 24. Specific functionalities are accessible from web pages similar to the web pages of FIGS. 11A and 11B are as follows:

Alarms and Status Data

Authorized end users can view data from many monitors 18 and test point monitors 24 at once using a network view web page or they can go to detailed status screens showing the condition of every monitored channel at individual pipeline testing sites. Along with channel conditions, important data such as communication metrics and historical alarm and notification data are available. Through data entry screens available to system administrators, channel names, alarm nomenclature, engineering units, and other site-specific data is entered into the network.

E-mail Alarm Notification

Alarms and automatic voltage readings can cause automatic e-mail notifications to be triggered to any number of recipients. E-mail addressees may be ranked by priority and different timing criteria may be established allowing secondary notification to alternate groups if any alarm condition persists beyond a desired limit. E-mails contain a URL (an Internet link) that when selected with a mouse click, brings up a web page specific to any one of monitors 18 and test point monitors 24. The user can then examine the detailed view of the monitor for channel condition verification or for activation of output functions. In addition to e-mail notification, alarms may be routed to recipients using alphanumeric pagers and facsimile devices. In all cases, the channel names and other nomenclature programmed into the data base through the Internet by the system administrator becomes the "vocabulary" used by the server to compose messages for the various notification and display schemes.

Administrative Functions

A comprehensive set of administrative functions and procedures provide users with complete control over all aspects of the pipeline monitoring system operation. Designated system administrators can control the level of access by their users. Individual users can configure the type and detail of information viewable at various levels of view depth. Built-in procedures also monitor all aspects of pipeline monitoring system performance on a real-time basis. Any system anomalies, security breaches, or perceived degradation of communication functions are immediately made available to system administrators via the same notification schemes used for actual alarms and status reporting—over e-mail, fax, and pocket pager. The system also provides information when any of monitors 18 and test point monitors 24 have not reported in with a health check message at the appointed time, providing another level of system integrity confirmation.

Report Generation

A full suite of automated reports is available through web pages allowing the user to analyze network and unit performance and to summarize alarm data on a periodic basis. All polling and control activity is identified by precise time and date stamps, along with an indication of which user performed the activity. Monitors 18 and test point monitors 24 are programmable to take readings and forward summaries to recipients, allowing daily reporting tasks to be automated. User-selectable report templates allow users to organize data in a variety of ways—facilitating the task of collecting voltage and current data from cathodic protection rectifiers to assure proper cathodic protection system performance.

By utilizing a centralized database and data center to route messages and to monitor and direct cathodic protection system operation, additional relevant external data may be accessed and delivered to the end user. For example, when an alarm situation has been detected and alarm and status data pertaining to the situation has been delivered to the end user through any of the means described herein, the centralized database application can access additional sources of data. In one embodiment, the application can access existing high resolution satellite and aerial photographic data which is displayed overlaid with alarm and status data, and any other pipeline test data, received from system monitors 18 and test point monitors 24. Such a display operates to serve as an additional resource in analyzing problems relating to cathodic system operation and aspects of a response to the problem, for example, surrounding structures and geographic features. At such time as satellite image providers allow satellites and orbiting cameras to be tasked by third party users, more recent images may be requested at the time of the alarm activity to show, for example, potential consequences of pipeline damage and pipeline easement encroachment, faster than travel to the site where the monitors sending the alarm could allow.

Figure 12:
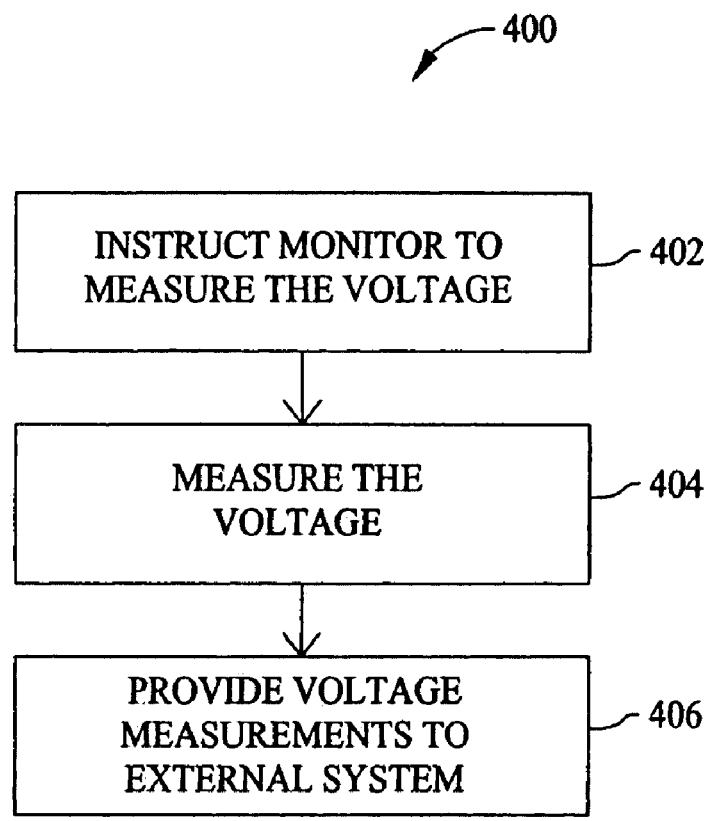
FIG. 12 is a flowchart illustrating a method implemented by test point monitors.

FIG. 12 is a flowchart of a voltage measurement method 400 implemented by monitors 18 and test point monitors 24 (shown in FIG. 1). The method is similar in that both monitors 18 and test point monitors 24 are measuring voltages, although monitor 18 is typically measuring an output of a cathodic protection rectifier 12 and test point monitor 24 measures a voltage present at a test point 14 along a pipeline. First, a monitor is instructed 402 to measure voltages. The monitor measures 404 the voltages, and provides 406 the voltage measurements to an external system as herein described.

Figure 13:
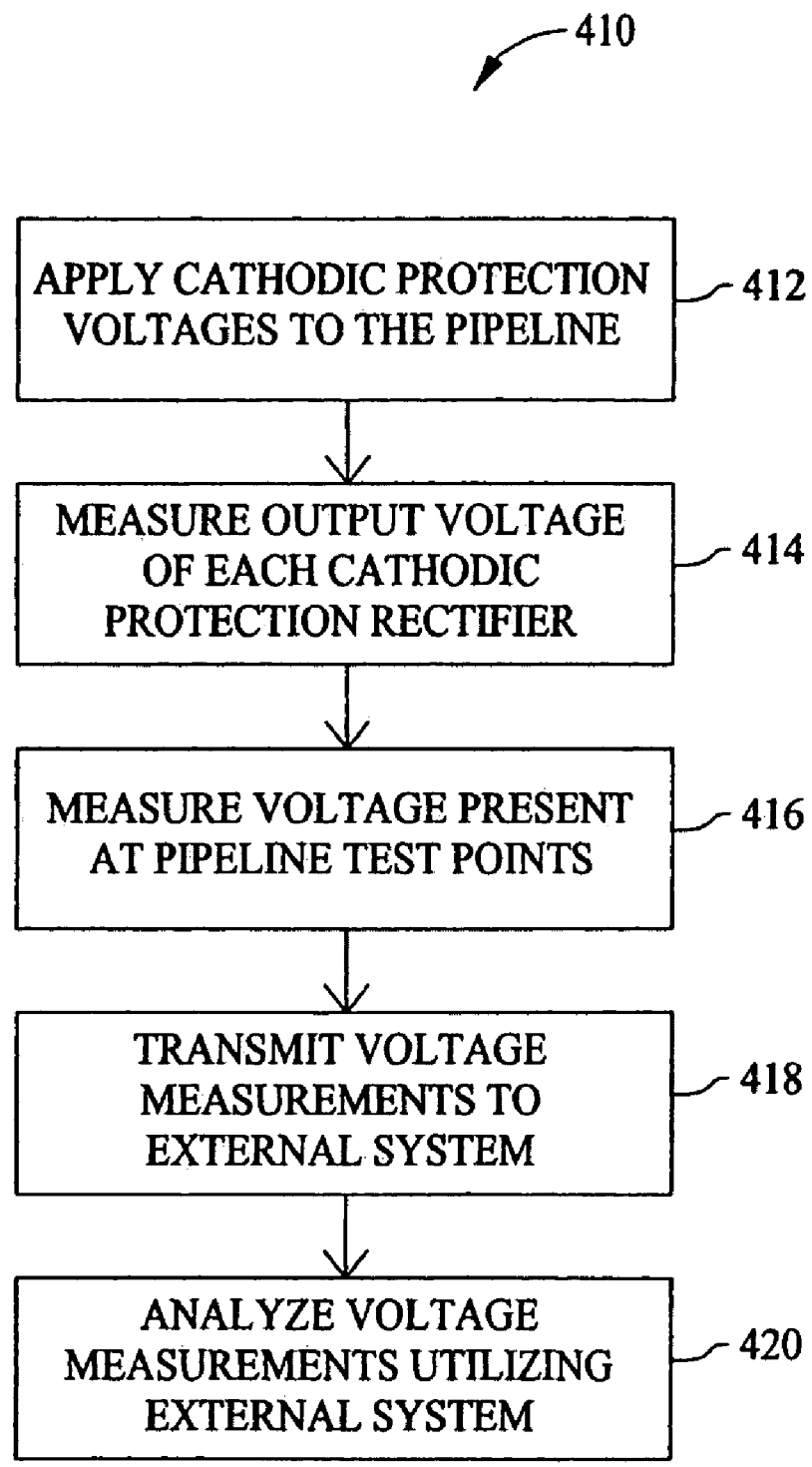
FIG. 13 is a flowchart illustrating a method for testing effectiveness of galvanic corrosion mitigation equipment installed along underground pipelines.
Figure 14:
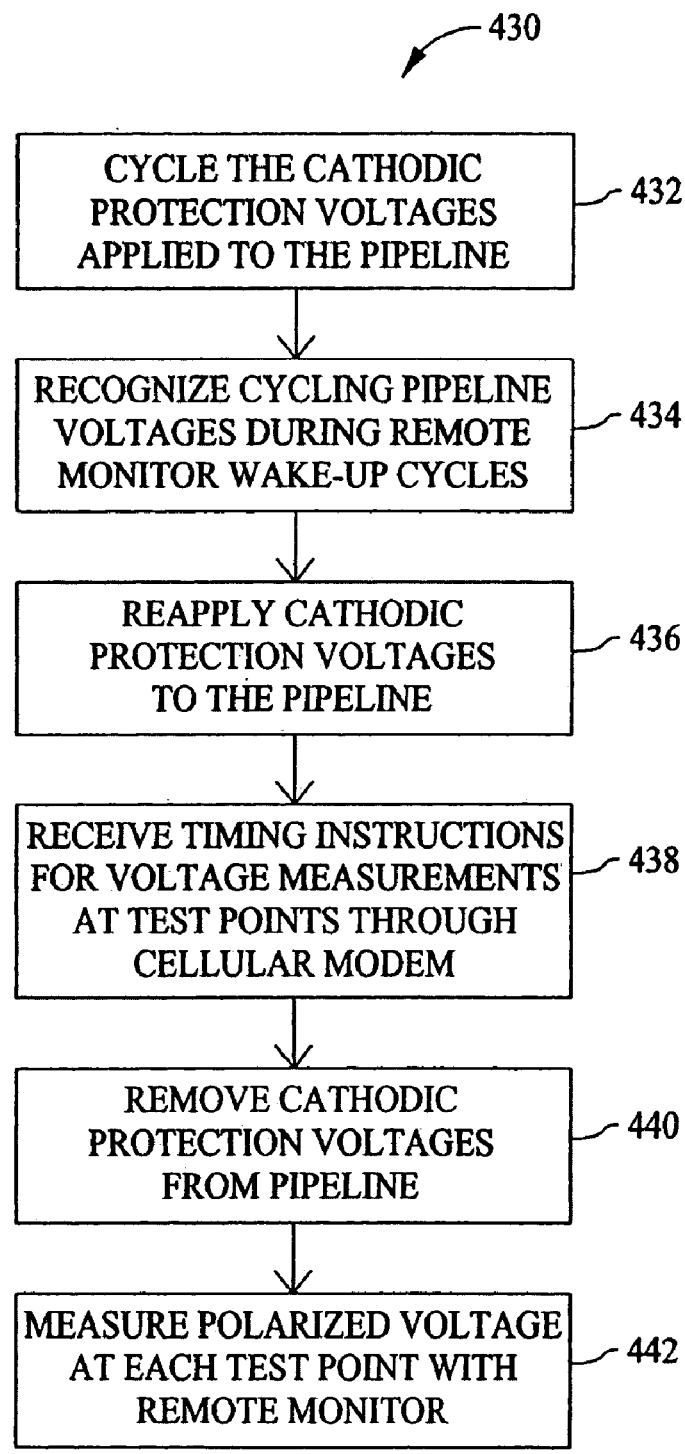
FIG. 14 is a flowchart illustrating a method of obtaining polarized voltage measurements along the pipeline.

FIG. 13 is a flowchart of a method 410 for testing effectiveness of galvanic corrosion mitigation equipment, as described above, installed along underground pipeline. The method is incorporated utilizing cathodic system monitors 18 and test point monitors 24, (shown in FIG. 1) where cathodic system monitors 18 are configured with a switching device to control application and removal of a voltage to the pipeline, supplied by cathodic protection rectifier 12. First, cathodic protection rectifier voltages are applied 412 to the pipeline and an output voltage of each cathodic protection rectifier is measured 414. Each test point 14 (shown in FIG. 1) is measured 416 for a voltage, the voltage being measured by test point monitors 24 located at each test point 14. The voltage measurements are transmitted 418 to the external system and are analyzed 420 utilizing the external system.

FIG. 13 is a flowchart illustrating a method 430 of obtaining a polarized voltage of the pipeline. It is to be recognized that the illustrated method 430 can be incorporated with method 410 illustrated in FIG. 12. To implement method 430 test point monitors 24 at test points 14 are configured with a wake-up mode controlled by a real time clock. First, the cathodic protection rectifier voltages on the pipeline are cycled 432. The voltage cycling is then recognized 434 at each test point 14 during wake-up cycle of each test point monitor 24. The cathodic protection rectifier voltages are re-applied 436 to the pipeline. Concurrently, each test point monitor 24 receives 438 a time to make a voltage measurement at the respective test point 14 through its cellular modem. Shortly before that time, the cathodic protection rectifier voltages are removed 440 from the pipeline and a polarized voltage is measured 442 at each test point 14.

Use of cathodic system monitors 18 and test point monitors 24, as described above, provides an economical solution to the described problems of synchronization of cathodic protection rectifiers 12, when performing "instant off" or polarized portions of close interval surveys by incorporating the Internet and cellular telephone networks 100. Further pipe-to-soil voltage tests at test points 14 are accomplished without having survey teams physically present at the test points 14. The combination of test point monitors 24 and the pipe further provide a means of delivering alarms from pipe-to-soil testing to end users, including instant off testing.

Such testing methodologies provide for a cost effective and accurate testing, which is important to pipeline companies which operate pipelines, that can stretch many miles in length and incorporate dozens of cathodic protection rectifiers 12 and test points 14, thereby replacing days of manual surveying done by testing teams, and therefore allowing for more frequent pipe-to-soil testing, including testing which incorporates synchronized turning off and on of cathodic protection rectifiers 12.

While described above with respect to cellular control channel communications, the methods and systems described above are implemented, in alternative embodiments, with other communications methodologies, for example, short messaging service (SMS) cellular channels, and general packet radio service (GPRS).

SMS is a protocol for sending short (up to 160 characters) alphanumeric messages to and from wireless devices across networks such as Global System for Mobile communications or GSM, which offers SMS as a built-in subscriber service. In use, SMS is characterized by out-of-band packet delivery and low-bandwidth message transfer. Therefore, SMS provides a cost-effective way of sending short bursts of information across a cellular network. SMS messages typically pass through an SMS operations center, which operates in conjunction with a network carrier.

In utilizing SMS, a remote monitor (e.g., test point monitor 24) can organize alarm information and operational data in the form of text email messages, delivering this data through a centralized data center, for example, to server 164 (shown in FIG. 6) or directly to end user computers, cellular telephones, or email accounts. When SMS data is routed through a data center, additional information from a centralized database may also be attached, providing the end user with more (augmented) information and detail than can otherwise be cost effectively delivered through the SMS channel.

The General Packet Radio Service (GPRS) is a non-voice service that allows information to be sent and received across a mobile telephone network, supplementing circuit switched data and SMS. GPRS operates at higher data transfer rates, for example, about three times as fast as the data transmission speeds possible over fixed telecommunications networks and about ten times as fast as current Circuit Switched Data services on GSM networks. GPRS facilitates instant connections whereby information can be sent or received, for example, from test point monitor 24, immediately as the need arises, subject to radio coverage.

GPRS involves overlaying a packet based air interface on the existing circuit switched GSM network, giving the user an option to use a packet-based data service. The information is split into separate but related "packets" before being transmitted and reassembled at the receiving end. Packet switching means that GPRS radio resources are used only when users are actually sending or receiving data. Rather than dedicating a radio channel to a mobile data user for a fixed period of time, the available radio resource can be concurrently shared between several users.

To utilize GPRS, alternative embodiments of the cathodic system monitors and test point monitors described herein incorporate a mobile phone or a terminal that supports GPRS, a subscription to a mobile telephone network that supports GPRS, and use of GPRS must be enabled for that user (although automatic access to GPRS may be allowed by some mobile network operators). Further, a destination to send or receive information through GPRS is needed. Whereas, with SMS this destination is often another mobile phone, in the case of GPRS, it is likely to be an Internet address, since GPRS is designed to make the Internet fully available to mobile users.

In utilizing GPRS, because GPRS can communicate using routable IP addresses, information on cathodic protection system operation can be delivered directly to a browser on a computer of an end user. To do so, an 'embedded server' (TCP/IP) stack is incorporated within one embodiment of the remote monitoring devices (cathodic system monitors 18 and test point monitors 24), and data presentations are established at the various monitors and delivered over the GPRS communication channel directly into an internet browser application. A data center can also receive information, and monitor the performance of the remote monitor to provide back-up capabilities and to detect and compensate for communication latencies or other system-related performance problems.

While the invention has been described in terms of various specific embodiments, those skilled in the art will recognize that the invention can be practiced with modification within the spirit and scope of the claims.

What is claimed is:

1. A method for testing operation of a cathodic protection rectifier (CPR) electrically coupled to a pipeline and a reference point, the CPR configured to apply a voltage to the pipeline, a cathodic system monitor which includes a cellular modem and is configured to communicate with an external system and further configured to control and verify application of the voltage to the pipeline, said method comprising:

applying the CPR voltage to the pipeline through a shunt resistor;

periodically cycling the applied voltage;

measuring the voltage across the shunt resistor with the cathodic system monitor;

operating the cathodic system monitor to calculate a current applied to the pipeline by the CPR;

transmitting the current calculations to the external system; and analyzing the current calculations utilizing the external system.

2. A method according to claim 1 wherein operating the cathodic system monitor to calculate a current comprises verifying that the applied voltage is cycling.

3. A method according to claim 2 wherein said cycling the applied voltage comprises a portion of a synchronized interruption test.

4. A system for monitoring a critical bond electrically connecting separate underground structures, the underground structures each including corrosion mitigation equipment applying a voltage to the respective structure, said system comprising:

a shunt resistor electrically connected between the separate structures; and a monitor configured to periodically measure the voltage across the shunt resistor, said monitor comprising a processor and a cellular modem interfaced to said processor, said monitor further configured to transmit the measured voltages over at least one of a cellular control channel, a short messaging service cellular channel, and a general packet radio service.

5. A method for monitoring a critical bond between separate underground structures, the underground structures each including corrosion mitigation equipment applying a voltage to the respective structure, said method comprising:

electrically connecting a shunt resistor between the separate structures;

periodically measuring the voltage across the shunt resistor utilizing a monitor, the monitor configured to transmit the measured voltages over at least one of a cellular control channel, a short messaging service cellular channel, and a general packet radio service.

6. A method for monitoring operation of corrosion mitigation equipment applying an electrical voltage to a well casing, said method comprising:

periodically measuring the voltage applied to the well casing with a monitor;

transmitting, to a site remote from the monitor, the measured voltage utilizing at least one of a cellular control channel, a short messaging service cellular channel, and a general packet radio service;

receiving, at the remote site, the transmitted voltage measurement; and determining, using the transmitted voltage measurement, whether the corrosion mitigation equipment is operational.

7. A test point monitor configured to monitor operation of corrosion mitigation devices for underground structures and structures having ground contact, said monitor comprising:

a processor;

a cellular modem interfaced to said processor; and at least one analog sensor interfaced to said processor, said monitor configured with a wake-up cycle, and during the wake up cycle, said monitor configured to cause a connection to be made to a testing point for the corrosion mitigation device and configured to measure at least one voltage utilizing said sensor, said monitor further configured to transmit the at least one measured voltage utilizing said modem.

8. A test point monitor according to claim 7 wherein during said wake-up cycle, said monitor is configured to receive communications initiating a measurement or series of measurements to be taken utilizing said sensor.

9. A test point monitor according to claim 8 wherein the series of measurements are measurements taken after one or more voltages have been removed from the structure by the corrosion mitigation device, said test point monitor configured with a programmable delay, the measurements made after the programmable delay.

10. A test point monitor according to claim 7 comprising a plurality of analog sensors, wherein a portion of said analog sensors are electrically connected to measure a pipe-to-soil potential at a close interval survey test point with respect to a reference point for an underground pipeline.

11. A method for adjusting an output of a cathodic protection rectifier, the cathodic protection rectifier connected to a power source and configured to apply a voltage across the pipeline and a reference point in the soil, a cathodic system monitor coupled to the rectifier and further configured to control application of the voltage to the pipeline, the cathodic system monitor configured to communicate with an external computer system, said method comprising:

receiving at the monitor, a communication from the external system to adjust an output of the rectifier, utilizing at least one of a cellular control channel, a short messaging service cellular channel, and a general packet radio service;

operating the monitor to adjust the output of the rectifier;

operating the monitor to measure the adjusted output of the rectifier; and transmitting the measured output to the external computer system, utilizing at least one of a cellular control channel, a short messaging service cellular channel, and a general packet radio service.

12. A method according to claim 11 wherein the cathodic system monitor includes an output control circuit, a full scale output of the output control circuit correlated to a maximum voltage output of the rectifier.

13. A method according to claim 12 wherein said receiving at the monitor comprises receiving an instruction to set the output control circuit output to a specific value and said operating the monitor to adjust the output of the rectifier comprises setting the output control circuit output to the received specific value.

14. A method according to claim 11 wherein operating the monitor to measure the adjusted output of the rectifier comprises:

measuring the voltage output by the rectifier; and
measuring the current supplied by the rectifier.

15. A method according to claim 11 wherein an output of the rectifier is connected to the pipeline through a shunt resistor, wherein measuring the current supplied by the rectifier comprises:

operating the monitor to measure the voltage across the shunt resistor; and determining the current supplied based on the voltage across the shunt resistor.

16. A cathodic protection rectifier system for an underground pipeline, the pipeline configured with a plurality of test points along a length of the pipeline, each electrically connected to the pipeline, said system comprising:

at least one cathodic rectifier coupled to a power source and configured to apply a voltage across the pipeline and a reference point in the soil;

a cathodic system monitor coupled to said rectifier, said monitor configured to control the voltage said rectifier applies to the pipeline, said monitor further configured to measure voltages and currents applied to the pipeline and to communicate the voltage and current measurements as pipeline test data, said monitor configured to control a switch located between said rectifier and the pipeline; and a computer system configured to receive the pipeline test data from said cathodic system monitor.

17. A cathodic protection rectifier system according to claim 16 wherein said monitor is configured to control the voltage said rectifier applies to the pipeline based on a communication received from said computer system.

18. A cathodic protection rectifier system according to claim 17 wherein said monitor comprises an output control circuit and the communication received from said computer system is configured to set an output of said output control circuit, the voltage applied by said rectifier to the pipeline scaled to the output of said output control circuit.

19. A cathodic protection rectifier system according to claim 18 wherein said output control circuit comprises an analog-to-digital converter.

20. A cathodic protection rectifier system according to claim 16 wherein said monitor and said computer system are configured to communicate utilizing at least one of cellular control channel communications, short messaging service cellular communications, and a general packet radio service.

21. A cathodic protection rectifier system according to claim 16 wherein said computer system is configured to:

access one or more of high resolution satellite data and aerial photographic data; and display the accessed data overlaid with pipeline test data.

22. A cathodic protection rectifier system according to claim 21 wherein said computer system is configured to:
  request updated data relating to one or more of satellite data and aerial photographic data upon receipt of pipeline test data; and
  display potential consequences relating to the pipeline based on the received pipeline test data and the requested, updated data.

23. A test point monitor comprising:
  a processor;
  a cellular modem interfaced to said processor; and
  at least one sensor interfaced to said processor, said monitor configured to cause a connection to be made to a testing point to monitor operation of corrosion mitigation equipment for one or more of well casings, critical bonds between two or more underground structures, and underground pipelines, said monitor further configured to transmit data relating to the operation of the corrosion mitigation equipment utilizing said modem.

* * * * *